(12) United States Patent
Ruben et al.

(10) Patent No.: US 7,016,752 B1
(45) Date of Patent: Mar. 21, 2006

(54) METHOD OF AND SYSTEM FOR LABELING CONTAINERS OF PRESCRIBED MEDICINE

(75) Inventors: Dennis Ruben, Lincolnwood, IL (US); Allen Yeung, Addison, IL (US)

(73) Assignee: Rxperts, Inc., Glenview, IL (US)

( * ) Notice: Subject to any disclaimer, the term of this patent is extended or adjusted under 35 U.S.C. 154(b) by 0 days.

(21) Appl. No.: 09/466,282

(22) Filed: Dec. 17, 1999

(51) Int. Cl.
*G06F 19/00* (2006.01)

(52) U.S. Cl. ................ 700/117; 700/231; 283/70; 283/81; 283/900; 206/534

(58) Field of Classification Search ............ 700/90, 700/117, 231, 235, 237; 283/70, 75, 67, 900; 221/5; 206/534, 538; 600/300
See application file for complete search history.

(56) References Cited

U.S. PATENT DOCUMENTS

| | | | | |
|---|---|---|---|---|
| 4,730,849 A | * | 3/1988 | Siegel | 283/70 |
| 4,732,411 A | * | 3/1988 | Siegel | 283/75 |
| 4,918,604 A | * | 4/1990 | Baum | 221/5 |
| 5,174,451 A | * | 12/1992 | Niven | 206/534 |
| 5,390,796 A | * | 2/1995 | Kerfoot, Jr. | 206/534 |
| 5,642,906 A | * | 7/1997 | Foote et al. | 283/67 |
| 5,842,976 A | * | 12/1998 | Williamson | 600/300 |
| 5,905,652 A | * | 5/1999 | Kutsuma | 700/235 |

FOREIGN PATENT DOCUMENTS

WO         WO99/17218      * 4/1999

* cited by examiner

*Primary Examiner*—Albert W. Paladini
*Assistant Examiner*—Steven R. Garland
(74) *Attorney, Agent, or Firm*—Winston & Strawn LLP

(57) ABSTRACT

A method of and system for labeling containers of prescribed medicine is provided wherein a photograph of a patient is taken using a camera. The photograph is then stored on a computer as a computer software object. When a prescription is filled for the patient, the photograph is printed on the label along with prescription information and the label is attached to the container.

10 Claims, 4 Drawing Sheets

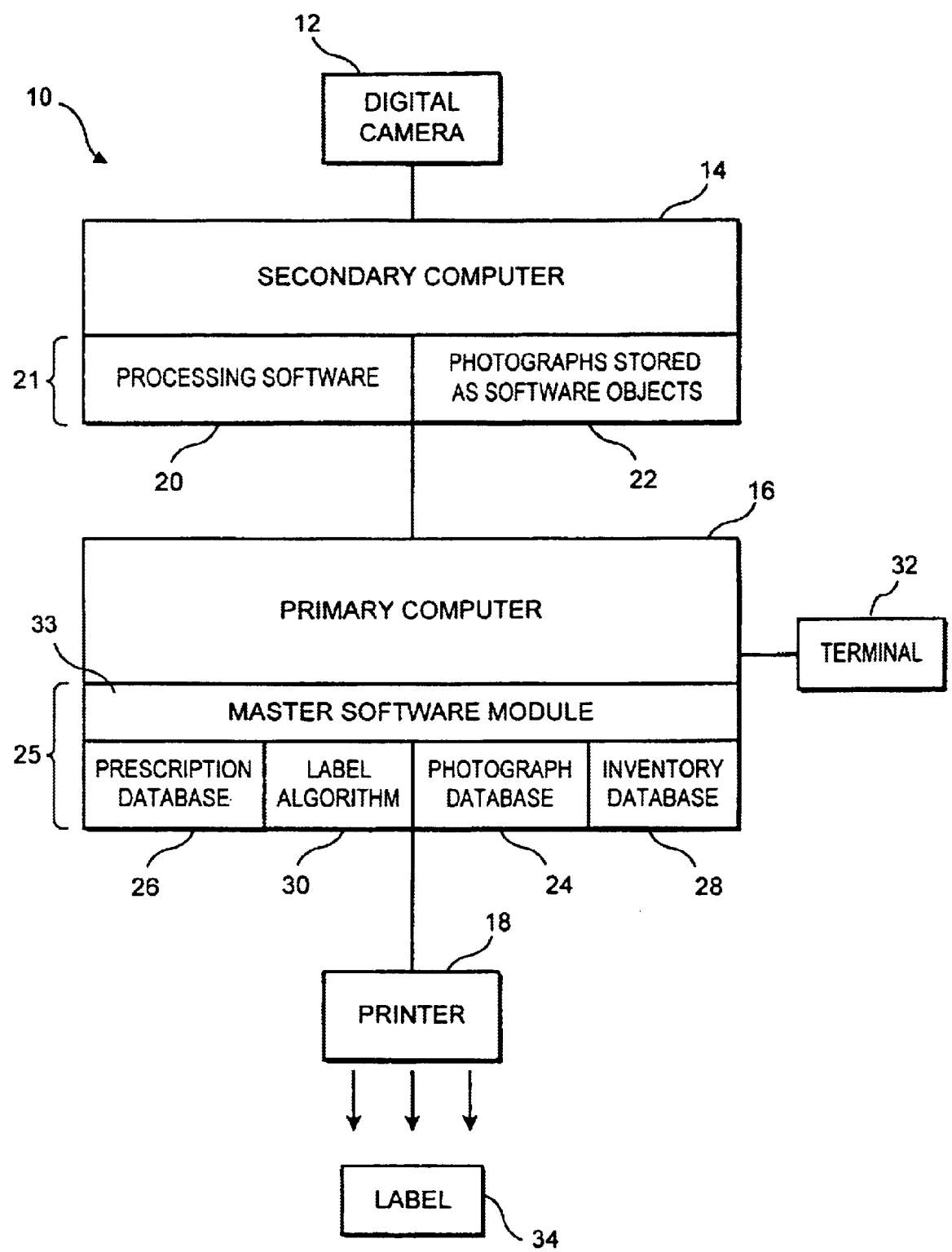
F I G. 1

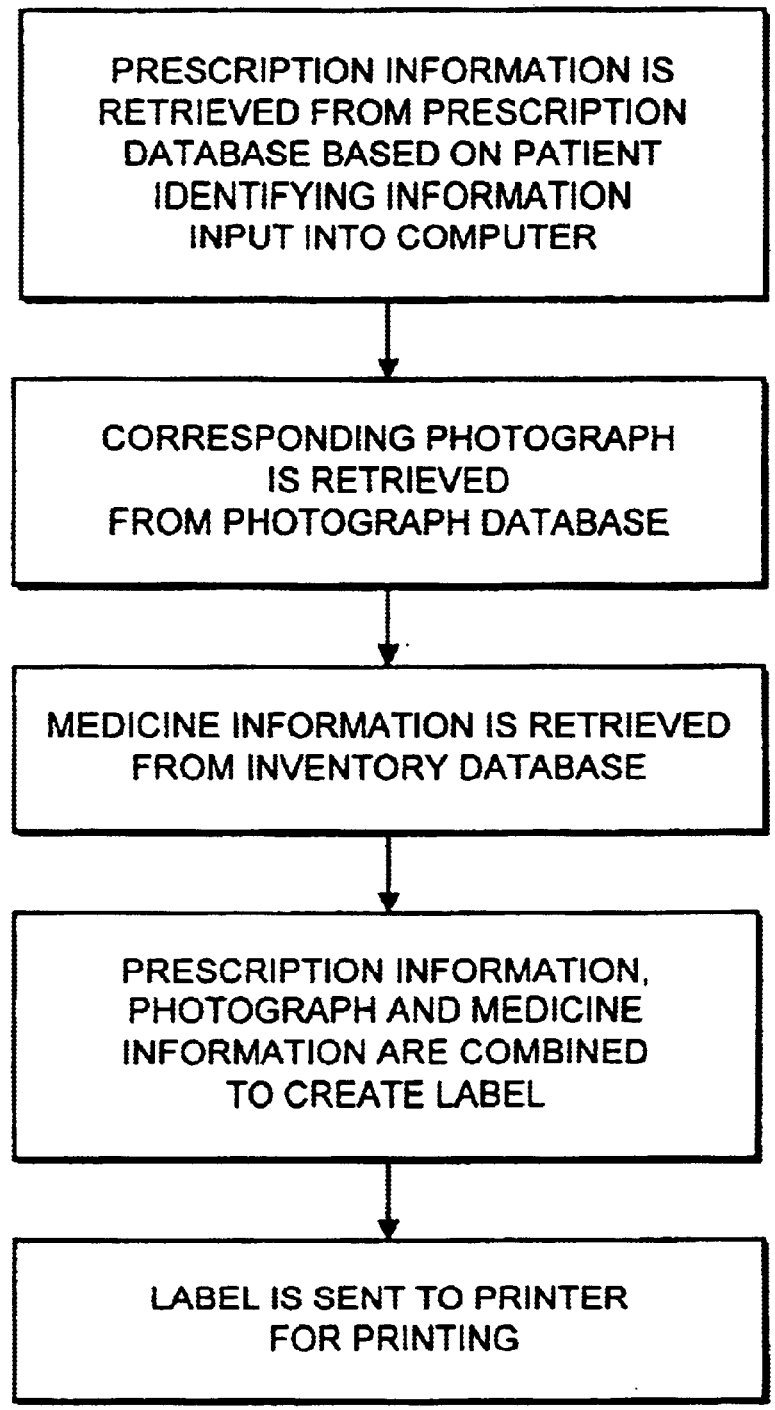
F I G. 3

US 7,016,752 B1

METHOD OF AND SYSTEM FOR LABELING CONTAINERS OF PRESCRIBED MEDICINE

BACKGROUND OF THE INVENTION

1. Field of the Invention

The present invention relates to prescription medicine. More particularly, the present invention relates to a method of and system for labeling containers of prescribed medicine.

2. Description of the Prior Art

Those of ordinary skill in the art and laypersons alike are well aware of labels which are found on containers of prescribed medicine. Typically, a label on a container of prescribed medicine will contain information such as the name of the patient; the name of the medicine and the dosage particulars; the name of the prescribing doctor; the quantity of medicine in the container; the expiration date of the medicine; a code which identifies the medicine manufacturer; a prescription number; the prescription date; the name and address of the pharmacy which filled the prescription; and a UPC code which can be used by the pharmacy to automatically identify the prescription in its computer system.

Despite the specific patient identifying information found on containers of prescribed medicine, when distributing medicine to a large number of patients, such as in hospitals and nursing homes, patients often receive the wrong medicine. To combat this serious problem, some hospitals and nursing homes take photographs of their patients and include the photographs in the medication administration record (MAR) used to record the administration of medicine. In this way the nurses administering the medicine are provided with means to help ensure that a patient does not receive the wrong medication. These photographs are also sometimes attached to the medication cart itself, such as on a drawer, or on the divider cards used to segregate the patients' medicine. These methods, however, are laborious, time consuming, highly inefficient and potentially dangerous.

SUMMARY OF THE PRESENT INVENTION

Accordingly, it is an object of the present invention to provide a method of and system for labeling containers of prescribed medicine which overcomes the problems associated with the prior art. It is a further object of the present invention to provide a method of and system for labeling containers of prescribed medicine wherein the label includes a photograph of the patient.

The foregoing and other objects are achieved by providing a method of and system for labeling containers of prescribed medicine wherein a photograph of a patient is taken. The photograph is then stored on a computer as a computer software object. When a prescription is filled for the patient, the photograph is printed on the label along with the patient's prescription information and the label is attached to the container.

The present invention will now be described in greater detail, with frequent reference being made to the drawings identified below.

BRIEF DESCRIPTION OF THE DRAWINGS

In the accompanying drawings:

FIG. 1 is a schematic diagram of a labeling system in accordance with the present invention;

FIG. 3 is a flow chart which illustrates the operation of the label algorithm.

DETAILED DESCRIPTION OF THE PREFERRED EMBODIMENT

Figure 2:
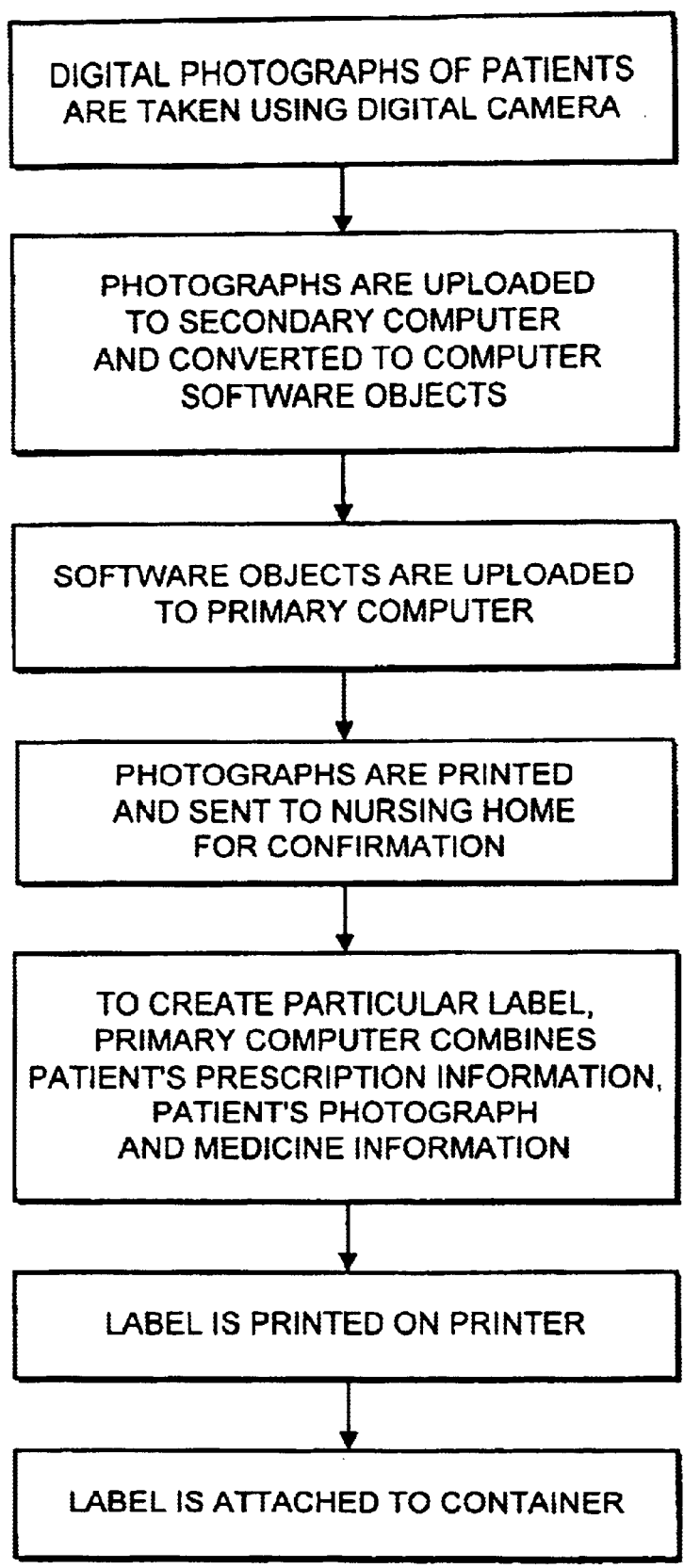
FIG. 2 is a flow chart which illustrates the operation of the labeling system of FIG. 1.

The following description is presented to enable any person of ordinary skill in the art to make and use the present invention. Various modifications to the preferred embodiment will be readily apparent to those of ordinary skill in the art, and the principles defined herein may be applied to other embodiments and applications without departing from the spirit and scope of the present invention. Thus, the present invention is not intended to be limited to the embodiment shown, but is to be accorded the broadest scope consistent with the principles and features disclosed herein.

The present invention is designed specifically for use by pharmacies which distribute prescriptions to patients in nursing homes, hospitals, or other large medical institutions. However, it will be realized by those of ordinary skill in the art that the present invention may be used by any pharmacy in distributing prescribed medicine. Thus, the present invention is in no way limited to use in nursing homes and hospitals.

Referring to FIG. 1, the system 10 in accordance with the present invention includes a digital camera 12 for taking digital photographs of the patients, such as a Kodak™ digital camera; a secondary computer 14, such as an IBM compatible personal computer, for downloading the digital photographs from the digital camera 12 and converting the photographs into software objects; a primary computer 16, such as a midrange computer, for creating the labels; and a printer 18 attached to the primary computer 16 for printing the labels.

For purposes of this discussion, it will be assumed that the system 10 will be used by a pharmacy to distribute medicine to patients in a nursing home.

Referring to FIG. 2, using the digital camera 12, a pharmacist, or an agent or employee of the pharmacist, first takes a digital photograph of each nursing home patient. The digital camera 12 is then attached, via an appropriately configured port, to the secondary computer 14 which contains processing software 20 stored in a memory 21 for converting the digital photographs into software objects 22, such as JPEG files. The photographs are then uploaded to the secondary computer 14 from the digital camera 12 and converted into software objects 22. Digital cameras are generally sold with processing software which will run under popular operating systems, such as Windows 95™, which do this conversion. Depending on the number of patients and the capacity of the digital camera 12, this process may need to be repeated a number of times. Additionally, as new patients enter the nursing home, their photographs must be taken as well.

After conversion, the software objects 22 are temporarily stored on the secondary computer 14 in memory 21. It will be realized by those of ordinary skill in the art that the secondary computer 14 may be any type of computer which is capable of performing the functions described herein. However, the secondary computer 14 will typically be an inexpensive IBM™ compatible personal computer having a central-processing-unit (CPU), a hard drive for storing the processing software and the software objects, a randomaccess-memory (RAM), a read only memory (ROM), a monitor, a keyboard and a mouse, all running under Windows 95™ or the like.

The software objects are next uploaded from the secondary computer 14 to the primary computer 16 via appropriately configured ports on each computer, where they are indexed and stored in a photograph database 24 which is stored in a memory 25. The primary computer 16 also includes stored in memory 25 a prescription database 26 which contains the prescription information of each patient, including the name of the patient, the name of the medicine and the dosage particulars, the name of the prescribing doctor, the name of the nursing home and the quantity of medicine in the prescription, and an inventory database 28 which contains information relating to the medicine which the pharmacist has in stock, including the identity of the manufacturers and the expiration date of the various medicines. The prescription database 26 and the inventory database 28 will be periodically updated as the prescription information of the patients change and as the pharmacist's inventory changes. The primary computer 16 also includes a label algorithm 30 which will create the labels.

While the primary computer may also be an IBM™ compatible computer, it will generally be a more business oriented computer, such as an IBM AS/400™, having a more powerful CPU, more RAM, more ROM, and a hard drive having sufficient memory to hold the various databases described herein. It will be apparent to those of ordinary skill in the art, however, that the primary computer 16 may be any type of computer capable of performing the functions described herein.

Before any prescriptions are filled, the photographs should be confirmed by sending a grid sheet having the name and photograph of every patient to the nursing home, who will ensure that the names and photographs are correctly matched. In this way any errors which may have occurred during the photographing process can be corrected.

When it comes time to fill a prescription for a patient, a pharmacist or a pharmacist's technician or the like will run the label algorithm 30 using a terminal 32 connected to the primary computer 16. Typically, the label algorithm 30 will be launched through a master software module 33 which is used to control the overall operation of the primary computer 16, including updating of the various databases. Such master software modules are commercially available and are well known to those of ordinary skill in the art.

Referring to FIG. 3, which illustrates how the label algorithm functions, the pharmacist or pharmacist's technician or the like will enter information which identifies the patient, such as the patient's name or a prescription number. The label algorithm 30 will then retrieve the prescription information from the prescription database 26, the corresponding photograph from the photograph database 24 and the medicine information from the inventory database 28 and combine the data to create a label. The label will then be printed on the printer 18, which is preferably a laser printer for clarity, but which may be any type of printer. The printed label is then attached to the medicine container, preferably through an adhesive on the back of the label. It will be appreciated that a label algorithm in accordance with the present invention may be readily implemented by one of ordinary skill in the art.

Figure 4:
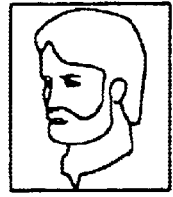
FIG. 4 is a sample label in accordance with the present invention.

A sample label 34 in accordance with the present invention is shown in FIG. 4. As is clear from FIG. 4, the label contains a photograph of the patient, as well as the patient's prescription information. Additionally, the label contains the expiration date of the medicine; a code which identifies the medicine manufacturer; the name and address of the pharmacy which filled the prescription; and a UPC code generated by the label algorithm 30 which can be used by the pharmacy to automatically identify and track the prescription.

It will be realized by those of ordinary skill in the art that the functions performed by the primary and secondary computers may in fact be performed on one computer instead of two, and thus the present invention is not limited to two separate computers. It will also be realized by those of ordinary skill in the art that the present invention is also not limited to use of a digital camera. For example, photographs may be taken using an ordinary camera. After developing, the photographs may be converted to computer software objects using a scanner or the like.

Nor, as discussed above, is the present invention limited to use in nursing homes, hospitals and the like. Rather, it will be apparent to those of ordinary skill in the art that the present invention may be used in any type of pharmacy, including a consumer's neighborhood pharmacy. For example, when a consumer goes to his neighborhood pharmacy to fill a prescription for the first time, the pharmacist can take his/her photograph and store the photograph in the pharmacist's computer. Each time the consumer fills a prescription, his/her photograph will be printed on the label.

Thus, in accordance with the foregoing the objects of the present invention are achieved. Modifications to the above would be obvious to those of ordinary skill in the art, but would not bring the invention so modified beyond the scope of the appended claims.

We claim:

1. A method of labeling a container of prescribed medicine, said method comprising the steps:

obtaining a photograph of a patient;

converting said photograph into a computer software object on a first computer;

storing on a second computer a prescription database of prescription information, an inventory database of medicine stock, and a photograph database of computer software objects of patient photographs that includes said computer software object of said patient photograph;

creating a label by retrieving and combining said computer software object of said patient from said photograph database, said prescription information of said patient from said prescription database, with medicine information from said inventory database;

printing said label;

attaching said label to said container;

storing on said second computer a plurality of computer software objects converted from photographs of patients of a nursing home; and sending a grid of photographs of said nursing home patients to said nursing home for verification.

2. The method of claim 1 further comprising sending a set of the stored photographs from the photograph database and matching patient names to a nursing facility for those patients for verification.

3. The method of claim 2 wherein the sending comprises sending the set of stored photographs and the matching patient names to a nursing home for the elderly.

4. The method of claim 2 further comprising sending patient-related prescription information in association with the set of photographs for verification.

5. The method of claim 2 further comprising printing the set of stored photographs and matching patient names for use in sending the set of stored photographs and matching patient names for verification.

6. The method of claim 2 wherein the sending comprises sending a grid comprising the set of patient photographs and the matching patient names.

7. The method of claim 1 further comprising receiving verification from said nursing home.

8. The method of claim 1 further comprising receiving patient names in connection with the photographs from said nursing home.

9. The method of claim 1 further comprising delivering labeled containers produced by the creating to supply patients of the said nursing homes with their prescribed medication.

10. A system for labeling a container of prescribed medicine, said system comprising:

a camera for taking a photograph of a patient;

a first computer for converting said photograph into a computer software object;

a second computer, distinct from said first computer, for creating a label containing prescription information of said patient and said photograph, wherein said second computer includes a prescription database of prescription information, includes a photograph database of computer software objects of patient photographs, and an inventory database of medicine stock, and is configured to create the label by retrieving and combining said computer software object of said patient's photograph from said photograph database, said prescription information of said patient from said prescription database with medicine information from said inventory database; and the second computer is further configured to generate a set of the stored photographs from the photograph database and matching patient names for use in verification at a nursing facility for those patients whereby the second computer generates a grid comprising the set of patient photographs and the matching patient names; and a printer for printing said label.

* * * * *